United States Patent

Hagen et al.

Patent Number: 5,216,171
Date of Patent: Jun. 1, 1993

[54] 2-AMINO-4-TRICHLOROPYRIDINE DERIVATIVES

[75] Inventors: Helmut Hagen, Frankenthal; Hans Ziegler, Mutterstadt; Juergen Pfister, Speyer; Gerhard Nilz, Dannstadt-Schauernheim; Gisela Lorenz, Neustadt; Juergen Dressel, Neuhofen, all of Fed. Rep. of Germany

[73] Assignee: BASF Aktiengesellschaft, Ludwigshafen, Fed. Rep. of Germany

[21] Appl. No.: 681,254

[22] Filed: Apr. 8, 1991

[30] Foreign Application Priority Data

Apr. 23, 1990 [DE] Fed. Rep. of Germany ....... 4012831

[51] Int. Cl.[5] .................... A01N 43/40; C07D 213/75
[52] U.S. Cl. .................... 546/309; 504/249; 504/250; 504/251; 504/253; 504/230; 504/195; 504/260; 504/252; 504/225; 504/235; 504/236; 504/238; 504/239; 504/242; 106/900; 544/130; 544/212; 544/238; 544/333; 546/22; 546/193; 546/262; 546/273; 546/277; 546/278; 546/279; 546/275; 546/280; 546/281; 546/283; 546/284; 546/304; 546/305; 546/306; 546/312
[58] Field of Search ............... 546/304, 305, 309, 306, 546/193, 262, 277, 278, 279, 280, 281, 283, 284; 71/94; 544/130, 212, 238, 333

[56] References Cited

U.S. PATENT DOCUMENTS

4,699,983 10/1987 Hagen et al. ............... 546/272
4,797,407 1/1989 Baker et al. ............... 546/309
4,992,503 2/1991 Baker et al. ............... 546/309

OTHER PUBLICATIONS

Chemical Abstracts, vol. 71, No. 19, Abstract No. 100,927s Nov. 10, 1969, p. 252.
Chemical Abstracts, vol. 82, No. 24, Abstract No. 170724z Jun. 16, 1975, p. 522.
Chemical Abstracts, vol. 84, No. 25, Abstract No. 175,143k, Jun. 21, 1976, p. 174.

Primary Examiner—C. Warren Ivy
Assistant Examiner—James H. Turnipseed
Attorney, Agent, or Firm—Herbert B. Keil

[57] ABSTRACT

2-Amino-4-trichloromethylpyridines of the general formula I

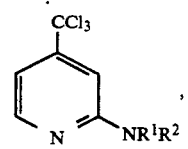

where
$R^1$ is hydrogen or $C_1-C_8$-alkyl,
$R^2$ is $C_1-C_8$-alkyl, $C_5-C_8$-cycloalkyl, $C_2-C_4$-alkenyl or phenyl, benzyl or phenylsulfonyl,
$-CX-R^3$, $-SO_2R^3$ or $-PX(OR^4)_2$ or
$R^1$ and $R^2$ together form $=CR^5R^6$ or $-CO-Z-CO-$,
X is oxygen or sulfur,
$R^3$ is $C_1-C_{20}$-alkyl, $C_2-C_6$-alkenyl, amino, $C_1-C_6$-alkylamino, di-$C_1-C_6$-alkylamino, morpholino, piperidino, pyrazolidino or $C_1-C_8$-alkylcarbonylamino, substituted or unsubstituted phenylamino or benzylamino,
$R^4$ is $C_1-C_8$-alkyl, $C_1-C_8$-haloalkyl or substituted or unsubstituted phenyl,
$R^5$ is hydrogen, $C_1-C_4$-alkyl, or substituted or unsubstituted phenyl,
$R^6$ is substituted or unsubstituted phenyl,
Z is substituted or unsubstituted ethylene which may be part of a substituted or unsubstituted cycloalkyl or cycloalkylene radical, substituted or unsubstituted ethenylene which may be part of a substituted or unsubstituted aromatic or heteroaromatic ring, and Z is not part of an unsubstituted phenyl radical, agriculturally useful salts thereof, processes for their preparation and the use thereof as nitrification inhibitors.

2 Claims, No Drawings

2-AMINO-4-TRICHLOROPYRIDINE DERIVATIVES

The present invention relates to 2-amino -4-trichloromethylpyridines of the general formula I

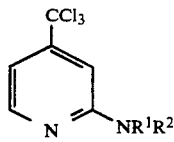

where $R^1$ is hydrogen or $C_1-C_8$-alkyl, $R^2$ is $C_1-C_8$-alkyl, $C_5-C_8$-cycloalkyl, $C_2-C_4$-alkenyl or phenyl, benzyl or phenylsulfonyl, where the aromatic radical in turn may be monosubstituted to pentasubstituted by halogen and monosubstituted to trisubstituted by the following groups: $C_1-C_4$-alkyl, $C_1-C_4$-haloalkyl, $C_1-C_4$-alkoxy, $C_2-C_4$-haloalkoxy and $C_1-C_4$-alkylthio, or —CX—$R^3$, —$SO_2R^3$ or —PX($OR^4$)$_2$ or $R^1$ and $R^2$ together form =$CR^5R^6$ or —CO —Z— CO—, X is oxygen or sulfur, $R^3$ is $C_1-C_{20}$-alkyl, $C_2-C_6$-alkenyl, amino, $C_1-C_6$-alkylamino, di-$C_1-C_6$-alkylamino, morpholino, piperidino, pyrazolidino or $C_1-C_8$-alkylcarbonylamino, phenylamino or benzylamino, whee the aromatic rings in turn may carry from one to five halogen atoms and from one to three of the following groups: $C_1-C_4$-alkyl, $C_1-C_4$-haloalkyl, $C_1-C_4$-alkoxy, $C_1-C_4$-haloalkyl and $C_1-C_4$-alkylthio or phenyl or a 5-membered or 6-membered hetaryl radical which may contain from one to three nitrogen atoms and one oxygen or sulfur atom or may contain one oxygen or sulfur atom, where the aromatic rings in turn may carry from one to five halogen atoms and from one to three of the following groups: nitro, $C_1-C_4$-alkyl, $C_1-C_4$-haloalkyl, $C_1-C_4$-alkoxy, $C_1-C_4$-haloalkoxy and $C_1-C_4$-alkylthio, $R^4$ is $C_1-C_8$-alkyl, $C_1-C_8$-haloalkyl or phenyl where the aromatic radical in turn may carry from one to five halogen atoms and from one to three of the following grouups: $C_1-C_4$-alkyl, $C_1-C_4$-haloalkyl, $C_1-C_4$-alkoxy, $C_1-C_4$-haloalkoxy and $C_1-C_4$-alkylthio, $R^5$ is hydrogen, $C_1-C_4$-alkyl or phenyl, where the aromatic radical in turn may carry from one to five halogen atoms and from one to three of the following groups: $C_1-C_4$-alkyl, $C_1-C_4$-haloalkyl, $C_1-C_4$-alkoxy, $C_1-C_4$-haloalkoxy and $C_1-C_4$-alkylthio, $R^6$ is phenyl which may carry from one to five halogen atoms and from one to three of the following groups: $C_1-C_4$-alkyl, $C_1-C_4$-haloalkyl, $C_1-C_4$-alkoxy, $C_1-C_4$-haloalkoxy, $C_1-C_4$-alkylthio, nitro and amino, and Z is an ethylene bridge which in turn may be part of a 5-membered or 6-membered cycloalkyl or cycloalkenyl radical, where this radical may carry from one to four halogen atoms and $C_1-C_4$-alkyl groups or an ethenylene bridge which may be part of a 5-membered or 6-membered aromatic or heteroaromatic ring, where this radical in turn may carry from one to four halogen atoms and one or two of the following groups: $C_1-C_4$-alkyl, $C_1-C_4$-haloalkyl, $C_1-C_4$-alkoxy, $C_1-C_4$-haloalkoxy, $C_1-C_4$-alkylthio and $C_1-C_4$-haloalkylthio, and Z is not unsubstituted phenyl, and their agriculturally useful salts.

The present invention furthermore relates to a process for the preparation fo the compunds I and their use, and the use of 2-N-phthalimido-4-trichloromethylpryidine (Ia) as a nitrification inhibitor.

DE-A 35 09 860 discloses the synthesis of 2-amino -4trichloromethylpyridine (II) from 2-N-phthalimido -4-trichloromethylpyridine (Ia) and the use of II as a nitrification inhibitor.

Nitrification inhibitors inhibit the oxidation of ammonium to nitrate in the soil for a certain time. Consequently, during this time there is no nitrate there to be taken up by the plants and stored under unfavorable conditions, nor to be displaced into deeper soil layers and from there into the groundwater. Ammonium is taken up by plants in the same way as nitrate and, being a cation, is subject to sorption in the soil.

However, 2-amino-4-trichloromethylpyridine (II) has an unsatisfactory action.

It is an object of the presnet invention to find and synthesize compounds which have improved properties with regard to their action as nitrification inhibitors.

We have found that this object is achieved by the 2-amino-4-trichloropyridine derivatives I defined at the outset. We have furthermore found processes for the preparation of these compounds and methods for inhibiting nitrification with these compounds.

The novel 2-amino-4-trichloromethylpyridine derivatives I are obtainable by various methods.

For example, the compounds I in which $R^1$ is hydrogen are preferably obtained by reacting 2-amino -4-trichloromethylpyridine II with an electrophilic reagent of the formula III in a conventional manner (Houben-Weyl, Methoden der organischen Chemie, Vol. 8, pages 653-713 (1952)) in an inert aprotic nonpolar organic solvent in the presence of a base.

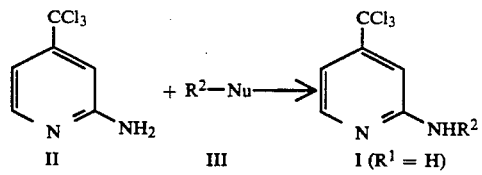

In formula III, Nu is a nucleophilic leaving group, such as halogen, eg. fluorine, chlorine or bromine or iodine, preferably chlorine or bromine.

The reaction is carried out in general at from 0° to 150° C., preferably from 50° to 100° C.

Particularly suitable solvents are chlorobenzene, o-dichlorobenzene and nitrobenzene, based such as triethylamine and diisopropylethylamine being employed, or basic solvents, such as pyridine or quinoline.

The educts II and III are usually used in a molar ratio of from 1 to 4, preferably from 1 to 2, mole equivalents.

The componds I are also obtained by reacting 2-chloro-4-trichloromethylpyridine IV with an amine V in a conventional manner in an inert polar solvent.

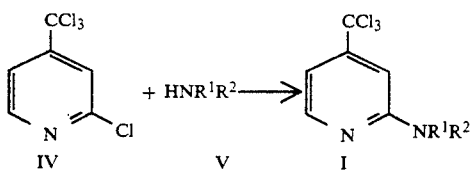

The reaction is carried out in general at from 0° to 150° C., preferably from 50° to 100° C.

Particularly suitable solvents are chlorobenzene, o-dichlorobenzene and nitrobenzene, bases such as triethylamine or diisopropylethylamine being used, or basic solvents, such as pyridine or quinoline.

The educts IV and V are usually used in a molar ratio of from 1 to 4, preferably from 1 to 2, mole equivalents.

Compounds I in which $R^1$ and $R^2$ together form $=CR^5R^6$ are preferably obtained by condensing 2-amino -4-trichloropyridine II with an aldehyde or ketone VI in a conventional manner (Houben-Weyl, Methoden der organischen Chemie, Vol. 11/2, pages 73–98 (1958)) in an inert aprotic nonpolar organic solvent in the presence of a catalyst.

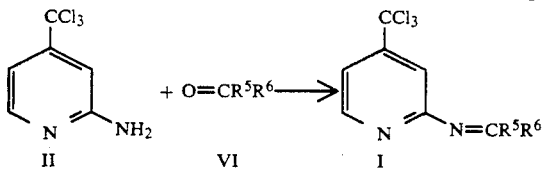

This reaction is carried out in general at from 20° to 200° C., preferably at the boiling point of the solvent.

Particularly suitable solvents are benzene, toluene, xylene, chlorobenzene and nitrobenzene.

Suitable catalysts are piperidinium acetate, ethyldiammonium diacetate, β-alanine and p-toluenesulfonic acid.

The educts are ususally used in a ratio of from 1 to 4, preferably from 1 to 1.5, mole equivalents, based on II.

Compounds I in which $R^1$ and $R^2$ together form —CO—Z—CO— are preferably obtained by condensing 2-amino-4-trichloromethylpyridine II in a conventional manner (Houben-Weyl, Methoden der organischen Chemie, Vol. 8, pages 656–657 (1952)) in an inert aprotic nonpolar organic solvent with a corresponding anhydride V, with removal of he water formed.

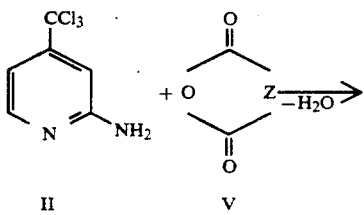

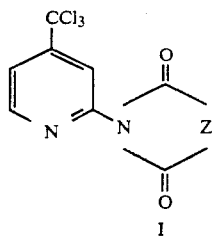

The reaction takes place in general at from 50° to 200° C., preferably form 100° to 150° C., or at the boiling point of the solvent.

Particularly suitable solvents are benzene, toluene, xylene, chlorobenzene, o-dichlorobenzene and nitrobenzene.

The educts are usually reacted in a ratio of from 1 to 3, preferably from 1 to 1.5, mole equivalents, based on II.

In view of the intended use of the 2-amino -4-trichloromethylpyridines I as nitrification inhibitors, preferred substituents are the following radicals:

$R^1$ is hydrogen or alkyl, such as methyl, ethyl, propyl, 1-methylethyl, butyl, 1-methylpropyl, 2-methylpropyl or 1,1-dimethylethyl, in particular methyl;

$R^2$ is alkyl as stated in general and in particular for $R^1$, cycloalkyl, such as cyclopentyl or cyclohexyl, alkenyl, such as ethenyl, 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl -2-butenyl, 1-methyl-3-butenyl, 2-methyl-3-butenyl, 3-methyl-3-butenyl, 1,1-dimethyl-2-propenyl, 1,2-diemthyl 1-propenyl, 1,2-dimethyl-2-propenyl, 1-ethyl-1-propenyl, -1-ethyl-2-propenyl, 1-hexenyl, 2-hexenyl, 3-hexenyl, 4-hexenyl, 5-hexenyl, 1-methyl-1-pentenyl, 2-methyl -1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl -3-butenyl, 1,2-diemthyl- 1-butenyl, 1,2-dimethyl-2-butenyl, 1,2-dimethyl -3-butenyl, 1,3-dimethyl-1-butenyl, 1,3-dimethyl-2-butenyl, 1,3-dimethyl-3-butenyl, 2,2-dimethyl-3-butenyl, 2,3-dimethyl -1-butenyl, 2,3-dimethyl-2-butenyl, 2,3-dimethyl-3-butenyl, 3,3-dimethyl-1-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl -1-methyl-2-propenyl, 1-ethyl -2-methyl-1-propenyl and 1-ethyl-2-methyl -2-propenyl, in particular 2-propenyl; phenyl, benzyl or phenylsulfonyl, where the aromatic radicals in turn may be monosubstituted to pentasubstituted by halogen, such as fluorine, chlorine, bromine or iodine, in particular chlorine or bromine and/or monosubstituted to trisubstituted by the following groups:

alkyl of 1 to 4 carbon atoms as stated for $R^1$, in particular methyl;

haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro- 2,2-di-fluoroethyl, 2,2-dichloro-2-fluoroethyl, 2,2,2-trichloroethyl or pentafluoroethyl, in particular trichloromethyl; alkoxy, such as methoxy, ethoxy, propoxy, 1-methylethoxy, butoxy, 1-methylpropoxy, 2-methylpropoxy or 1,1-dimethylethoxy, in particular methoxy;

haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoromethoxy;

methylthio, ethylthio, propylthio, 1-methylethylthio, butylthio, 1-methylpropylthio, 2-methylpropylthio or 1,1-dimethylethylthio, in particular butylthio;

—CX—$R^3$, —SO$_2$$R^3$ or PX(O$R^4$)$_2$, or $R^1$ and $R^2$ together form =C$R^5$$R^6$ or —CO—Z—CO—;

X is oxygen or sulfur;

$R^3$ is alkyl as stated for $R^1$ or heptyl, 1-methylhexyl, 2-methylhexyl, 3-methylhexyl, 4-methylhexyl, 5-methylhexyl, 1-ethylpentyl, 2-ethylpentyl, 3-ethylpentyl, 4,4-dimethylpentyl, 1-ethyl-1-methylbutyl, octyl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylhexyl, 4-ethylhexyl, 5,5-dimethylhexyl, nonyl, 1-methyloctyl, 2-methyloctyl, 3-methyloctyl, 4-methyloctyl, 5-methyloctyl, 6-methyloctyl, 7-methyloctyl, 1-ethylheptyl, 2-ethylheptyl, 3-ethylheptyl, 4-ethylheptyl, 5-ethylheptyl, 6,6-dimethylheptyl and quindecyl, in particular 2,2-dimethylproply;

alkenyl as stated for $R^2$, in particular 2-propenyl; amino;

alkylamino, such as methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 1,2-dimethylpropylamino, 1,1-dimethylpropylamino, 2,2-dimethylpropylamino, 1-ethylpropylamino, hexylamino, 1-methylpentylamino, 2-methylpentylamino, 3-methylpentylamino, 4-methylpentylamino, 1,2-dimethylbutylamino, 1,3-dimethylbutylamino, 2,3-dimethylbutylamino, 1,1-dimethylbutylamino, 2,2-dimethylbutylamino, 3,3-dimethylbutylamino, 1,1,2-trimethylpropylamino, 1,2,2-trimethylpropylamino, 1-ethylbutylamino, 2-ethylbutylamino and 1-ethyl-2-methylpropylamino, in particular butylamino;

dialkylamino, such as dimethylamino, diethylamino, dipropylamino and dibutylamino, in particular diethylamino; morpholino; piperidino; pyrazolidino; phenylamino or benzylamino, where the aromatic rings in turn may carry from one to five halogen atoms, in particular fluorine and chlorine and/or from one to three of the following groups: alkyl, haloalkyl, alkoxy, haloalkoxy and/or alkylthio, each of 1 to 4 carbon atoms, as stated above;

alkylcarbonylamino, such as acetylamino, propionylamino, butyrylamino, 2-methylpropionylamino, pentanoylamino, 2-methylbutyrylamino, 3-methylbutyrylamino, 2,2-dimethylpropionylamino, hexanoylamino, 2-methylpentanoylamino, 3-methylpentanoylamino, 4-methylpentanoylamino, 2,2-dimethylbutyrylamino, 2,3-dimethylbutyrylamino, 3,3-dimethylbutyrylamino or 2-ethylbutyrylamino;

phenyl or hetaryl, such as pyrrolyl, pyrazolyl, imidazolyl thiazolyl, furyl, isoxazolyl, oxazolyl, oxadiazolyl, thienyl, isothiazolyl, thiadiazolyl, pyridyl, pyrimidyl, pyrazinyl, pyridazinyl or triazinyl, where these aromatic radicals in turn may carry from one to five halogen atoms, in particular fluorine or chlorine, and/or from one to three of the following groups: alkyl, haloalkyl, alkoxy, haloalkoxy and/or alkylthio, each of 1 to 4 carbon atoms, as stated above;

$R^4$ is alkyl of 1 to 8 carbon atoms as stated for $R^3$, in particular methyl or ethyl;

haloalkyl, in particular as stated for $R^2$, or phenyl, where this aromatic radical in turn may carry from one to five halogen atoms, in particular fluorine or chlorine, and/or from one to three of the following groups: alkyl, haloalkyl, alkoxy, haloalkoxy and/or alkylthio, each of 1 to 4 carbon atoms, as stated above;

$R^5$ is hydrogen;

alkyl of 1 to 4 carbon atoms as stated for $R^1$, or phenyl, where this aromatic radical in turn may carry from one to five halogen atoms, in particular fluorine or chlorine, and/or from one to three of the following groups: alkyl, haloalkyl, alkoxy, haloalkoxy and/or alkylthio, each of 1 to 4 carbon atoms, as stated above;

$R^6$ is phenyl which may carry from one to five halogen atoms, in particular fluorine or chlorine, and/or from one to three of the following groups: nitro, amino, alkyl, haloalkyl, alkoxy, haloalkoxy or alkylthio, each of 1 to 4 carbon atoms, as stated above, and Z is ethylene which in turn may be part of a 5-membered or 6-membered cycloalkyl or cycloalkenyl radical, such as cyclopentyl, cyclohexyl, cyclopentenyl or cyclohexenyl, where this radical may carry from one to four halogen atoms, in particular chlorine or bromine, and/or from one to three alkyl groups of 1 to 4 carbon atoms as stated for $R^1$, in particular methyl, or ethenylene which may be part of a 5-membered or 6-membered aromatic or heteroaromatic ring as stated for $R^3$, where this radical in turn may carry from one to five halogen atoms, in particular fluorine or chlorine, and/or from one to three of the following groups: alkyl, haloalkyl, alkoxy, haloalkoxy and/or alkylthio, each of 1 to 4 carbon atoms, as stated above, and Z is not unsubstituted phenyl, and the agriculturally useful salts thereof.

The active ingredients can be applied to the soil area to be treated or can be mixed with fertilizers before application.

If the active ingredients are applied alone, applicaiton rates of active ingredient of from 0.01 to 20, preferably from 0.1 to 10, in particular from 1 to 5, kg/ha are preferable. When the active ingredient is applied together with fertilizers, the application rate of the active ingredient is determined by the amount of feritilizer nitrogen applied per ha. In general, from 0.01 to 10, preferably from 0.1 to 5, in particular from 1 to 3, % by weight, based on the amount of nitrogen applied per ha, are admixed.

No special formulations are required for the applicaiton of active ingredient and formulated fertilizer together. Synthesis Examples

EXAMPLE 1

2-Butyrylamino-4-trichloromethylpyridine

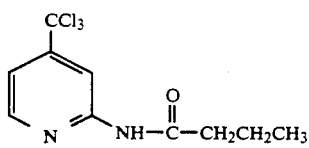

7.3 ml (0.07 mol) of butyryl chloride were added to 10.6 g (0.05 mol) of 2-amino -4-trichloromethylpyridine and 70 ml of pyridine at 0° C. while cooling with ice. After stirring for three hours at 25° C., the reaction mixture was added to 5% strength hydrochloric acid and this mixture was extracted with ether. 12.7 g (90%) of the product wre obtained from the organic phase. Mp.: 88°-90° C., Active ingredient Example 1.003

EXAMPLE 2

2-Methylaminocarbonylamino-4-trichloromethylpyridine

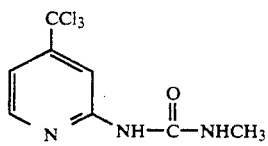

17 ml (0.3 mol) of methyl isocyanate and 1 ml of triethylamine were added to 21.2 g (0.1 mol) of 2-amino-4-trichloromethylpyridine and 400 ml of toluene at 25° C. After 4 hours at 80° C., the resulting solid was isolated. 21.8 g (82%) of the desired product were obtained. Mp.: 192°-195° C.; Active Ingredient Example 2.001

EXAMPLE 3

2-Diphenylphosphorylamino-4-trichloromethylpyridine

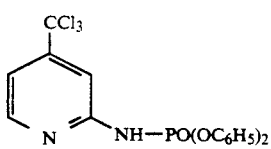

6.2 ml (0.03 mol) of diphenylphosphoryl chloride were added to 6.3 g (0.03 mol) of 2-amino -4trichloromethylpyridine and 60 ml of pryidine at 0° C. After 12 hours at 25° C., the reaction mixture was added to 200 ml of 5% strength hydrochloric acid. The colorless precipitate formed was isolated. 7.0 g (53%) of the desired product were obtained. Mp.: 134°-136° C.; Active Ingredient Example 1.016

EXAMPLE 4

2-(2,3-Dichlorophenylmethyleneamino)4-trichloromethylpyridine

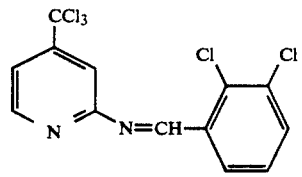

10.6 g (0.05 mol) of 2-amino -4-trichloromethylpyridine and 100 ml of toluene were heated at the boil with 10.5 g (0.06 mol) of 2,3-dichlorobenzaldehyde and 1 g of p-toluenesulfonic acid for 15 hours, water being distilled off. The resulting solution was then washed with sodium sulfite solution and with water. 13.7 g (75%) of the desired product were obtained from the organic phase. Mp.: 75°-78° C.; Active Ingredient Example 3.003

EXAMPLE 5

2-N-Succinimido-4-trichloromethylpyridine

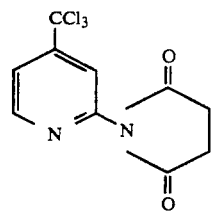

21.2 g (0.1 mol) of 2-amino-4-trichloromethylpyridine, 12.0 g (0.12 mol) of succinic anhydride and 500 ml of 1,2-dichlorobenzene were heated at the boil for 2 hours, water being distilld off. 19.0 g (65%) of the desired product were obtained from this reaction solution. Mp.: 139° C.; Active Ingredient Exmaple 4.001

The methods described in the above Synthesis Examples were used for the preparation of further compounds I, with appropriate modification of the educts. The compounds thus obtained are shown in the following Tables together with physical data.

TABLE 1

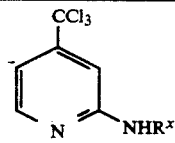

| No. | $R^x$ | phys. Data [mp (°C.); NMR (δ in ppm)] |
|---|---|---|
| 1.001 | COCH$_3$ | 2,15(s, 3H); 7.60(m, 1H); 8,53(d, 1H) 8.72(d, 1H); 11,0(s, 1H)-d$_6$-DMSO |
| 1.002 | COCH$_2$CH$_3$ | 105-107 |
| 1.003 | COCH$_2$CH$_2$CH$_3$ | 88-90 |
| 1.004 | COC(CH$_3$)$_3$ | 76-78 |
| 1.005 | COCH$_2$C(CH$_3$)$_3$ | 116-118 |
| 1.006 | COCH(CH$_2$CH$_3$)(CH$_2$)$_3$CH$_3$ | 102-104 |
| 1.007 | CO(CH$_2$)$_{14}$CH$_3$ | 66-67 |
| 1.008 | COC(CH$_3$)=CH$_2$ | 111-112 |

TABLE 1-continued
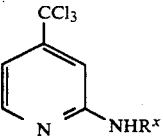
| No. | R$^x$ | phys. Data [mp (°C.); NMR (δ in ppm)] |
|---|---|---|
| 1.009 | 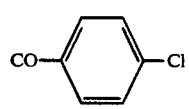 | 119–120 |
| 1.010 | 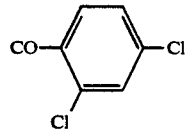 | 145–147 |
| 1.011 | 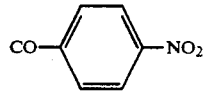 | 141–144 |
| 1.012 | 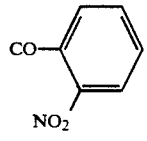 | 159–162 |
| 1.013 | 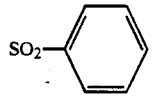 | 206 |
| 1.014 | 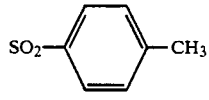 | 216 |
| 1.015 | 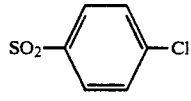 | 223 |
| 1.016 | PO(OC$_6$H$_5$)$_2$ | 134–136 |
| 1.017 | PO(OCH$_2$CH$_3$)$_2$ | 1,30(m, 6H); 4,00(m, 2H); 4,20(m, 2H); 6,98(m, 1H); 7,35(m, 1H); 7,85(m, 1H)-CDCl$_3$ |
| 1.018 | PS(OCH$_2$CH$_3$)$_2$ | 1,35(m, 6H); 4,25(m, 4H); 7,60(m, 1H); 800(m, 1H); 8,85(m, 1H)-CDCl$_3$ |
TABLE 2
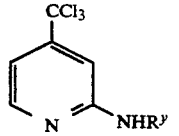
| No. | R$^y$ | phys. Data [mp (°C.); NMR (δ in ppm)] |
|---|---|---|
| 2.001 | CONHCH$_3$ | 192–195 |
| 2.002 | CONH(CH$_2$)$_3$CH$_3$ | 81–82 |
TABLE 2-continued
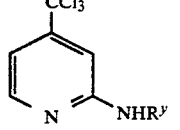
| No. | R$^y$ | phys. Data [mp (°C.); NMR (δ in ppm)] |
|---|---|---|
| 2.003 | 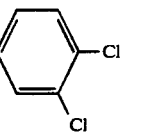 | >240 |

TABLE 2-continued

Structure: 4-CCl₃-pyridine-2-NHR^y

| No. | R^y | phys. Data [mp (°C.); NMR (δ in ppm)] |
|---|---|---|
| 2.004 | CSNH₂ | 207 |
| 2.005 | CSNH—CO—C₆H₅ | 148 |

TABLE 3

Structure: 4-CCl₃-pyridine-2-N=CH-C₆H₄-R^z

| No. | R^z | phys. Data [mp (°C.); NMR (δ in ppm)] |
|---|---|---|
| 3.001 | H | 130-132 |
| 3.002 | 4-Cl | 129-131 |
| 3.003 | 2,3-Cl,Cl | 75-78 |
| 3.004 | 2,4-Cl,Cl | 105-107 |
| 3.005 | 2,6-Cl,Cl | 7,35(m, 1H); 7,48(m, 1H); 7,70(m, 1H); 7,85(m, 1H); 8,30(d, 1H); 8,65(d, 1H); 9,62(s, 1H)-CDCl₃ |
| 3.006 | 3,4-Cl,Cl | 73-75 |
| 3.007 | 4-OCH₃ | 3,90(s, 3H); 7,85(d, 2H); 7,95(d, 2H); 8,15(d, 1H); 8,58(d, 1H); 9,12(s, 1H); 9,88(s, 1H)-CDCl₃ |
| 3.008 | 4-NO₂ | 138-139 |

TABLE 4

Structure: 4-CCl₃-pyridine-2-N(CO-)(CO-)Z (imide)

| No. | Z | phys. Data [mp (°C.); NMR (δ in ppm)] |
|---|---|---|
| 4.001 | —CH₂CH₂— | 139 |
| 4.002 | cyclohexenyl (1,2-disubst., 4-ene) | 140 |
| 4.003 | cyclohexenyl (1,2-disubst., 1-ene) | 90-92 |
| 4.004 | 3,4-dimethylphenyl | 138-140 |

TABLE 4-continued

| No. | Z | phys. Data [mp (°C.); NMR (δ in ppm)] |
|---|---|---|
| 4.005 | 4-Cl-phenyl (3-Me) | 66-69 |
| 4.006 | 4-C(CH₃)₃-phenyl (3-Me) | 105-110 |

USE EXAMPLES

Investigation of the Inhibition of the Nitrification in Soil and of the Reduction of the Nitric Content in Plants.

A comparison of the nitrification action of the novel compound No. 1.004 and of the known nitrification inhibitor A (2-amino-4-trichloromethylpyridine) is given below.

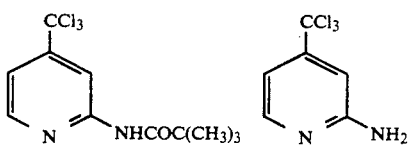

Example No. 1.004    A

In each of the experiments, 1 ppm of active ingredient and 220 mg of ammonium sulfate (=46.6 mg of N) were mixed with 200 g of a soil adjsuted to 50% of the maximum water capacity and the soil was incubated at 20° C. After four, six and eight weeks, the ammonium still present in the soil was determined and the results were expressed relative to the amount used at the beginning.

The experiments for the reduction of the nitrate content in plant material were carried out in Mitscherlich vessels which held 6.5 kg of soil. The soil was mixed with 1 g of N as ammonium sulfate plus 1% (based on the amount of N used) of active ingredient and was kept in the vessel initially at 40% of the maximum water capacity for the entire test period and at 60% of the maximum water capacity after germination and growth of the plants. After reaching a ripeness suitable for consumption (technical ripeness), the plants wee harvested and the nitrate content determined. The results were stated in ppm of NO₃, based on fresh material. Spinach was used as the example plant.

The effect on nitrification in this soil is to be found in Table A, which shows that Example No. 1.004 resulted in 90% inhibition of nitrification over a period of eight weeks. The comparative compound A achieved only an inhibition of 58% over the same period. Without the active ingredient, as much as 90% of the NH4 nitrogen has been converted after four weeks.

The reduction in the nitrate content of spinach is shown in Table B. Starting from a nitrate content of 1203 ppm (spring) or 4203 ppm (fall), a substantial reduction in the nitrate values was achieved with both substances. Nevertheless, the reduction by Example No. 1.004 was more pronounced. The very low values of the experiment without N are unimportant since very low plant yields of unmarketable produce resulted.

TABLE A

Inhibition of nitrification of ammonium N by the addition of 1 ppm of active ingredient to the soil

| Example No. | Duration of action (%) | | |
|---|---|---|---|
| | 4 | 6 | 8 weeks |
| A | 95 | 94 | 58 |
| 1.004 | 100 | 95 | 90 |
| without active ingredient | 10 | 0 | 0 |

TABLE B

The effect of nitrification inhibitors on the nitrate content of spinach

| Example No. | Addition of N | Application rate of active ingredient/N | ppm of NO3 [based on the fresh material] | |
|---|---|---|---|---|
| | | | For spring | For fall |
| — | — | — | 36 | 121 |
| — | + | — | 1203 | 4203 |
| A | + | 1% | 424 | 1927 |
| 1.004 | + | 1% | 71 | 934 |

—: No ammonium sulfate
+: 1 g of N as ammonium sulfate

We claim:
1. A 2-amino-4-trichloromethylpyridine of the formula I

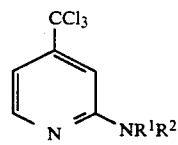

where
R$^1$ is hydrogen or C$_1$-C$_8$-alkyl,
R$^2$ is —CX—R$^3$,
X is oxygen or sulfur
R$^3$ is C$_1$-C$_{20}$-alkyl, C$_2$-C$_6$-alkenyl, amino, C$_1$-C$_6$-alkylamino, di-C$_1$-C$_6$-alkylamino, morpholino, piperidino, pyrazolidino or C$_1$-C$_8$-alkylcarbonylamino, or phenylamino or benzylamino, where the aromatic rings in turn may carry from one to five haolgen atoms and from one to three of the following groups: C$_1$-C$_4$-alkyl, C$_1$-C$_4$-haloalkyl, C$_1$-C$_4$-alkoxy, C$_1$-C$_4$-haloalkoxy and C$_1$-C$_4$-alkylthio, or phenyl, pyrrolyl, pyrazolyl, imidazolyl, thiazolyl, furyl, isoxazolyl, oxazolyl, oxadiazolyl, thienyl, isothiazolyl, thiadiazolyl, pyridyl, pyrimidyl, pyrazinyl, pyridazinyl or triazinyl, where the aromatic rings in turn may carry from one to five halogen atoms and from one to three of the following groups: nitro, C$_1$-C$_4$-alkyl, C$_1$-C$_4$-haloalkyl, C$_1$-C$_4$-alkoxy, C$_1$-C$_4$-haloalkoxy and C$_1$-C$_4$-alkylthio.

2. A 2-amino-4-trichloromethylpyridine of claim 1, wherein R$^1$ is hydrogen and R$^2$ is —CO—C(CH$_3$)$_3$.

* * * * *